United States Patent [19]

Wolberg et al.

[11] 4,309,419
[45] Jan. 5, 1982

[54] METHOD FOR THE INHIBITION OF IMMUNE RESPONSE

[75] Inventors: Gerald Wolberg; Thomas P. Zimmerman, both of Cary, N.C.

[73] Assignee: Burroughs Wellcome Co., Research Triangle Park, N.C.

[21] Appl. No.: 84,445

[22] Filed: Oct. 12, 1979

[30] Foreign Application Priority Data

Oct. 13, 1978 [GB] United Kingdom ............... 40447/78

[51] Int. Cl.$^3$ .................... A61K 31/70; C07H 19/16
[52] U.S. Cl. .................................. 424/180; 424/162; 536/24; 536/26
[58] Field of Search .................... 536/26, 24; 424/180, 424/162

[56] References Cited

U.S. PATENT DOCUMENTS 3,919,193  11/1975  Mian et al. ............................ 536/24
4,148,888  4/1979  Canteni et al. ....................... 424/180

OTHER PUBLICATIONS

Mizuno et al., "Chem. Abst.", vol. 70, 1969, p. 47771(n).
Borchart, et al., "Jour. of Medicinal Chem." vol. 17, #8, 1974, pp. 868–873.
Chiang, et al., "Molecular Pharmacology", 13 pp. 939–947, 1977.
Mizuuno, et al., "Chem. Pharm. Bull.", 16(10) pp. 2011–2017, 1968.
Chiang, et al. "Chem. Abst.", vol. 87, 1977, P 14799x.
Kredich, "Chem. Abst." vol. 88, 1978, P 69770k.

Primary Examiner—Johnnie R. Brown
Attorney, Agent, or Firm—Donald Brown

[57] ABSTRACT

Adenosine derivatives for inhibition of immune response are disclosed.

Adenosine derivatives of formula (I)

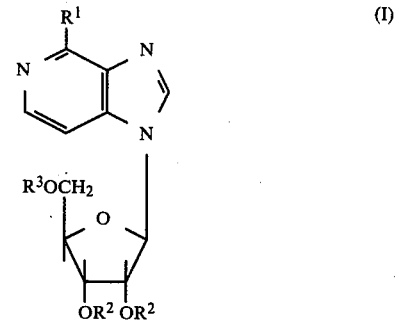

wherein
$R^1$ is amino or lower alkyl amino;
$R^2$ is hydrogen or an aliphatic carboxylic acid residue; and
$R^3$ is hydrogen, aliphatic carboxylic acid residue or a phosphoric acid residue, are useful as inhibitors of immune response. The activity is potentiated by derivatives of homocysteine and homocystine. Particularly useful is 3-deaza-adenosine both alone and in combination with L-homocysteine thiolactone, Pharmaceutical formulations of compounds of formula (I) alone and with potentiators are provided.

14 Claims, No Drawings

METHOD FOR THE INHIBITION OF IMMUNE RESPONSE

The present invention relates to adenosine derivatives, to formulations containing the derivatives and to the use thereof in medicine. More specifically the invention is concerned with 3-deazaadenosine and derivatives thereof, to formulations thereof and their use in medicine either alone or in conjunction with a potentiator.

It has previously been reported (Science, N.Y., 187, 957 (1975)) that adenosine is a potent inhibitor of leucocyte mediated cytolysis (LMC) and suggested that adenosine (present in the cells because of the absence of adenosine deaminase (ADA)) was responsible for combined immuno-deficiency disease. This indicated that adenosine and other inhibitors of LMC would be useful in medicine where it was desired to inhibit immune response.

It was later reported (*Federation Proceedings*, 35(3), 1213 (1976)) that a number of adenosine derivatives were also potent inhibitors of LMC. It was found that ability to inhibit LMC was related to the effect of these derivatives on the intracellular levels of cyclic AMP (cAMP). This observation applied equally to adenosine itself. Thus whilst the potent inhibitors of LMC also significantly increased the level of cAMP those which were inactive did not. Although a few compounds which did not increase cAMP levels did inhibit LMC the level of activity was very low and the disclosure suggested those compounds which increase cAMP are good LMC inhibitors whilst those that do not are inactive or only poor inhibitors of LMC.

A disadvantage of adenosine and a number of those derivatives which inhibit LMC is that they are substrates for adenosine deaminase (ADA) and require the presence of an ADA inhibitor for the full expression of biological activity. In the absence of such an inhibitor the rapid deactivation renders them much less active.

A further disadvantage of adenosine and those derivatives known as LMC inhibitors is that their mechanism of action is such as to lead to undesirable side-effects in view of the known effects of cyclic AMP on mammalian circulatory systems.

A yet further disadvantage of a number of the derivatives of adenosine which inhibit LMC is that, although they have high levels of activity, they are also relatively toxic and consequently have a poor therapeutic index.

It has also been reported (*Mol.Pharmacol*, 13, 939–947 (1977)) that 3-deazaadenosine is a potent inhibitor of S-adenosyl-L-homocysteine hydrolase and its activity was related to the equally potent effect of adenosine against the enzyme concerned. This same paper described 3-deazaadenosine as an analogue of biological potential and taught that the compound could inhibit cell transformation and virus production by Rous Sarcoma virus in vitro.

We have now surprisingly found that 3-deazaadenosine and derivatives thereof as defined in formula (I) below are potent inhibitors of LMC whilst not significantly affecting the levels of cyclic AMP. These compounds are not substrates for ADA.

Compounds of formula (I) are:

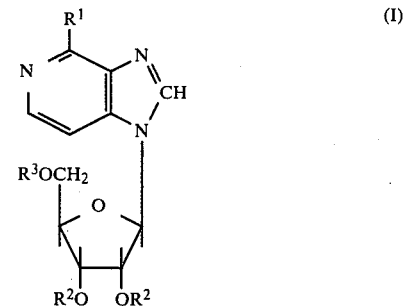

wherein
$R^1$ is amino or lower alkyl amino;
$R^2$ is hydrogen or an aliphatic carboxylic acid residue and
$R^3$ is hydrogen, an aliphatic carboxylic acid residue or a phosphoric acid residue.

As used herein the term lower alkyl refers to an alkyl group of from 1 to 4 carbon atoms.

The preferred compounds are those wherein $R^2$ and $R^3$ are both hydrogen.

Particularly preferred is 3-deazaadenosine, ($R^1=R^2=R^3=H$).

The compounds of formula (I) and their pharmaceutically acceptable salts are useful whenever it is desirable to suppress the immune response. Thus the compounds of formula (I) are, for example, useful in the treatment of autoimmune diseases such as Lupus erythematosis, Hemolytic anemia, Ulcerative Colitis and Nephrosis and in the prevention of rejection of foreign cells such as grafts including organ transplants.

The present invention therefore provides, in one aspect, a compound of formula (I) or a pharmaceutically acceptable salt thereof for use in medicine, in particular for the suppression of immune response.

The pharmaceutically acceptable salts are suitably acid addition salts.

The activity of the compounds of formula (I) resides in the free base and thus the nature of the acid participating in the acid addition salts is of minor importance. However, the salts are preferably derived from non-toxic acids. The acids used will normally be those recognised to be pharmaceutically acceptable acid addition salts.

Such acid addition salts include, for example, those derived from hydrochloric acid, hydroiodic acid, sulphuric acid, p-toluenesulphonic acid, methane sulphonic acid, maleic acid, lactic acid, citric acid, tartaric acid, succinic acid, oxalic acid, p-chlorobenzene-sulphonic acid, phosphoric acid, acetic acid, isethionic acid, gluconic acid, pantothenic acid and lactobionic acid.

While it is possible for the compounds of formula (I) to be administered as the raw chemical they are preferably presented in the form of a pharmaceutical formulation.

The invention therefore further provides a pharmaceutical formulation comprising an active compound together with a pharmaceutically acceptable carrier therefor. The carrier must be "acceptable" in the sense of being compatible with the other ingredients of the formulation and not deleterious to the recipient thereof.

The invention additionally provides a method for the preparation of a pharmaceutical formulation comprising bringing into association an active compound and a pharmaceutically acceptable carrier therefor.

The compounds of formula (I) may conveniently be presented in unit dosage form. A convenient unit dose formulation contains the active compound in an amount of from 5 mg to 1 g, preferably 25 mg to 500 mg, most preferably 100 to 300 mg.

The pharmaceutical formulations include those suitable for oral, rectal or parenteral (including intramuscular and intravenous) administration, although oral is the preferred route. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules, sachets or tablets each containing a predetermined amount of the active compound. A tablet may be made by compression or moulding, optionally with one or more accessory ingredients. Compressed tablets may be prepared by compressing in a suitable machine the compound of formula (I) in a free-flowing form such as a powder or granules optionally mixed with a binder, lubricant, inert diluent, lubricating, surface active or dispersing agent. Moulding tablets may be made by moulding an inert liquid diluent. Tablets may be optionally coated and, if uncoated, may be optionally scored. Capsules may be prepared by filling the compound of formula (I) either alone or in admixture with one or more accessory ingredients, into the capsule cases and then sealing them in the usual manner. Sachets are analogues to capsules wherein the active ingredients together with any accessory ingredient(s) are sealed in a rice paper envelope.

Pharmaceutical formulations suitable for oral administration wherein the carrier is a liquid may be presented as a solution or a suspension in an aqueous liquid or a non-aqueous liquid, or as an oil-in-water or water-in-oil liquid emulsion.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the compound of formula (I) with the softened or melted carrier(s) followed by chilling and shaping in moulds.

Pharmaceutical formulations suitable for parenteral administration include sterile solutions or suspensions of the compound of formula (I) in aqueous or oleaginous vehicles. Such preparations are conveniently presented in unit dose or multidose containers which are sealed after introduction of the formulation until required for use.

It should be understood that in addition to the aforementioned carrier ingredients the pharmaceutical formulations described above may include, as appropriate, one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

As has been described above the compounds of the present invention are useful as immunosuppressants. The invention thus further provides a method for suppressing the immune response in a mammal including man which comprises the administration of an immunosuppressive-effective amount of a compound of formula (I) or a pharmaceutically acceptable salt thereof.

The amount of compound of formula (I) required for therapeutic effect will of course vary not only with the particular compound but also with the route of administration. In general a suitable dose for the treatment of a mammal (including man) will lie in the range of from 0.3 to 100 mg per kilogram bodyweight (mg/kg), preferably in the range of 1.0 to 50 mg/kg, more preferably in the range of 2 to 15 mg/kg, per day during the period that inhibition of immune response is necessary.

It is know (*Cell,* 12, 931–938 (1977)) that the cytotoxic effect of adenosine towards lymphocytes is potentiated by L-homocysteine thiolactone and this disclosure suggested that such toxicity was related to combined immuno deficiency disease.

The LMC inhibitory effect of the compound of formula (I) is potentiated by a group of compounds comprising L-homocysteine, D-homocysteine, L-homocysteine thiolactone, D-homocysteine thiolactone, L-homocystine, D-homocystine and their selenium analogues, hereinafter referred to as the "potentiators".

Although such a potentiation by L-homocysteine thiolactone was to be expected for the LMC inhibitory effect of adenosine it was surprising in view of their evidently distinct mechanism of action to find that compounds of formula (I) were also potentiated.

The invention thus provides, in a further aspect a combination comprising a compound of formula (I) or an acid addition salt thereof together with a potentiator as defined hereinabove.

The preferred combination comprises 3-deazaadenosine and L-homocysteine thiolactone.

The combination is useful for the suppression of immune response and thus for the treatment of the conditions described above for which the compounds of formula (I) may be employed.

The compounds of formula (I) and the potentiator may be administered sequentially or simultaneously. Whilst these compounds may be administered as the raw chemicals they are preferably administered either in the same or separate pharmaceutical formulations.

When the compounds of formula (I) and the potentiator are administered in separate formulations the compound of formula (I) is suitably administered in a formulation as hereinbefore described.

In the case where the potentiator is administered as a separate formulation the formulation is suitably of the type described hereinbefore for the compounds of formula (I) and may be prepared by the methods described for such formulations. When administered separately the potentiator is conveniently in unit dosage form. A convenient unit dose formulation contains the potentiator in an amount of from 10 mg to 1 g.

Although the compounds of formula (I) and potentiators may be administered separately they are conveniently administered in a single formulation.

The invention thus additionally provides a pharmaceutical formulation comprising a compound of formula (I) (as herein defined) or pharmaceutically acceptable salt thereof and a potentiator (as herein defined) together with a pharmaceutically acceptable carrier therefor. The term "acceptable" is used in the sense in which it is defined hereinbefore.

The invention further provides a method of preparing such formulations which comprises bringing the compound of formula (I) and the potentiator into association with a pharmaceutically acceptable carrier therefor.

The formulations suitably contain the compound of formula (I) and potentiator in a ratio of from 1:100 to 1:10 preferably 1:50 to 1:20, more preferably 1:30 and may conveniently be presented in unit dosage form. A convenient unit dose formulation contains from 5 mg to 100 mg of the compound of formula (I) together with an amount of potentiator dictated by the aforementioned ratios and within the range of 50 mg to 1 g.

The formulations include those suitable for oral, rectal and parenteral (including intramuscular and intravenous) administration, although oral is the preferred route. Such formulations suitably are of the form for the compounds of formula (I) alone as hereinbefore described and may be prepared by analogous methods.

The invention therefor further provides a method for the inhibition of immune response in a mammal, including man, which comprises the administration of a compound of formula (I) (as herein defined) or pharmaceutically acceptable salt thereof in conjunction with an effective potentiating amount of a potentiator (as herein defined).

By the term "effective potentiating amount" is meant an amount of the potentiator which, when administered within an amount of a compound of formula (I) insufficient to inhibit immune response, increases the effect of the compound of formula (I) to a level where inhibition of immune response is achieved.

The amount of compound of formula (I) required will of course vary not only with the particular compound and the route of administration but also with the particular potentiator and the amount thereof administered. Preferably the compound of formula (I) is administered in an amount which, alone, would not effectively inhibit the immune response. The ratio of compound of formula (I) to potentiator administered is suitably in the range of 1:100 to 1:10, preferably 1:50 to 1:20, more preferably 1:30. Generally suitable doses for the inhibition of immune response in mammals, including man, will lie in the range of from 0.3 mg to 100 mg per kg body weight of a compound of formula (I) and from 3 mg to 1 g per kg, preferably 5 mg to 100 mg per kg, body weight of a potentiator per day during the period in which it is required to inhibit immune response.

The following Examples are given merely by way of illustration of the invention and should not be construed in any way as constituting a limitation thereof.

EXAMPLE 1

Assay of Lymphocyte mediated cytolysis (LMC) in vitro

The test compounds were assayed in vitro by the method described in Science, N.Y. 187, 957 (1975). The order of addition of reagents was (1) cytotoxic lymphocytes; (2) test compound dissolved in pyrogen-free saline; (3) $^{51}$Cr-labelled EL4 cells. In those experiments where an ADA inhibitor was required EHNA+ was added before step (2) to give a final concentration of 7.0 μM. The assay was performed in the absence or presence of L-homocysteine thiolactone (200 μM). The results are shown in Table 1 below.

TABLE 1

| Test Compound | Conc. (μM) | % lysis Reduction Alone | plus L-homocysteine thiolactone |
|---|---|---|---|
| Adenosine* | 18.8 | 59 | 100 |
|  | 9.4 | 59 | 94 |
| 2-Fluoro-adenosine | 2 | 60 | 72.9 |
|  | 1 | 48.9 | 64.6 |
| 2-Chloro-adenosine | 9.4 | 64.4 | 70.8 |
|  | 4.7 | 62.2 | 60.4 |
| 3-Deazaadenosine | 37.5 | 56 | 93 |
|  | 18.8 | 43 | 92 |

+ erythro-9-(2-hydroxy-3-nonyl)adenine
*tested in presence of ADA inhibitor

EXAMPLE 2

Effect of test compounds on levels of cyclic AMP

The level of cyclic AMP present in acid soluble extracts of lymphocytes was determined after 30 minutes incubation of the lymphocytes with the test compounds. The level of cyclic AMP was determined by known radioimmunoassay techniques after purification of the extracts on sequential columns of aluminium oxide and Dowex 1-X8 resin and subsequent 2'-O-succinylation of the resultant samples. The results obtained are given in Table 2 below.

TABLE 2

| Test Compound | Conc. (μM) | Percentage of control cell cAMP after 30 mins. incubation with test compound |
|---|---|---|
| Saline | — | 100 |
| Adenosine | 18.8 | 337 |
| 2-Fluoroadenosine | 4.7 | 185 |
| 2-Chloroadenosine | 18.8 | 479 |
| 3-Deazaadenosine | 50 | 90 |

EXAMPLE 3

Tablet

A tablet is prepared from the following ingredients:

|  | Amount per tablet |
|---|---|
| 3-Deazaadenosine | 200 mg |
| Lactose | 170 mg |
| Potatoe starch, dried | 28.6 mg |
| Magnesium stearate | 1.4 mg |
| Total | 400.0 mg |

EXAMPLE 4

Tablet

|  | Amount per tablet |
|---|---|
| 3-Deazaadenosine | 10 mg |
| L-Homocysteine thiolactone hydrochloride | 390 mg |
| Lactose | 160 mg |
| Potatoe starch, dried | 38 mg |
| Magnesium stearate | 2 mg |
| Total | 600 mg |

EXAMPLE 5

Suppository

| | Amount per suppository |
|---|---|
| 3-Deazaadenosine | 20 mg |
| L-Homocysteine thiolactone hydrochloride | 780 mg |
| Cocoa butter | 2000 mg |

EXAMPLE 6

Syrup

| | Amount per 10 ml |
|---|---|
| 3-Deazaadenosine | 10 mg |
| L-Homocysteine thiolactone hydrochloride | 390 mg |
| Glycerine | 1 g |
| Sucrose | 7 g |
| Methyl paraben | 10 mg |
| Sodium benzoate | 10 mg |
| Flavor, cherry | .01 ml |
| Coloring | q.s. |
| Water, purified | q.s. to 10.0 ml |

EXAMPLE 7

Injection

| | Amount per ampoule |
|---|---|
| 3-Deazaadenosine | 10 mg |
| L-Homocysteine thiolactone hydrochloride | 390 mg |
| Sodium chloride | 8.5 mg |
| Water for injection | q.s. to 1.0 ml |

We claim:

1. A method for the inhibition of immune response in a mammal comprising the administration, to a mammal in need thereof, of an immune response inhibiting, non-toxic amount of 3-deazaadenosine or a pharmaceutically acceptable salt thereof.

2. A method according to claim 1 wherein 3-deazaadenosine or a pharmaceutically acceptable salt thereof is administered in an amount of from 0.3 mg per kilogram bodyweight to 100 mg/kg bodyweight per diem.

3. The method of claim 1 in which the mammal is man.

4. The method of claim 1 or 3 in which the 3-deazaadenosine or salt is administered orally, rectally, or parenterally.

5. The method of claim 1 or 3 in which 3-deazaadenosine is administered.

6. The method of claim 1 or 3 in which 3-deazaadenosine is administered orally, rectally or parenterally.

7. A method for the inhibition of immune response in a mammal in need thereof which comprises the administration to said mammal of an immune response inhibition amount or less of 3-deazaadenosine or a pharmaceutically acceptable salt thereof together with a potentiator selected from the group consisting of L-homocysteine, D-homocysteine, L-homocysteine thiolactone, D-homocysteine thiolactone, L-homocystine, D-homocystine and their selenium analogues.

8. A method according to claim 7 in which the 3-deazaadenosine or a salt thereof is administered in an amount of from 0.3 mg to 100 mg per kilogram/bodyweight per diem and the potentiator is administered in an amount of from 3 mg to 1 g per kilogram per diem.

9. The method of claim 7 in which the mammal is man.

10. The method of claim 1 or 7 in which the mammal in need thereof is suffering from Lupus erythematosis, Hemolytic anemia, Ulcerative Colitis or Nephrosis.

11. The method of claim 7 in which the potentiator is L-homocysteine.

12. A pharmaceutical preparation for use in medicine which comprises a compound of 3-deazaadenosine or a pharmaceutically acceptable salt thereof together with a potentiating amount of L-homocysteine, D-homocysteine, L-homocysteine thiolactone, D-homocysteine thiolactone, L-homocystine, D-homoscystine and their selenium analogues, the amount of compound or salt to potentiator present is in the ratio of 1:100 to 1:10.

13. The preparation of claim 12 in which 3-deazaadenosine and L-homocysteine are in the preparation.

14. The preparation of claim 12 in which 3-deazaadenosine is in the preparation.

* * * * *